United States Patent
Es-Souni

(10) Patent No.: US 8,486,484 B2
(45) Date of Patent: Jul. 16, 2013

(54) IMPLANT COMPRISING A BIOTOXIC COATING AND METHOD FOR THE PRODUCTION THEREOF

(75) Inventor: Mohammed Es-Souni, Mielkendorf (DE)

(73) Assignee: Fachhochschule Kiel, Kiel (DE)

( * ) Notice: Subject to any disclaimer, the term of this patent is extended or adjusted under 35 U.S.C. 154(b) by 613 days.

(21) Appl. No.: 12/601,087

(22) PCT Filed: May 13, 2008

(86) PCT No.: PCT/DE2008/000814
§ 371 (c)(1),
(2), (4) Date: Nov. 20, 2009

(87) PCT Pub. No.: WO2008/145088
PCT Pub. Date: Dec. 4, 2008

(65) Prior Publication Data
US 2010/0152842 A1    Jun. 17, 2010

(30) Foreign Application Priority Data
May 26, 2007 (DE) .......................... 10 2007 023 294

(51) Int. Cl.
*A61L 33/00* (2006.01)
(52) U.S. Cl.
USPC ........ 427/2.24; 623/11.11; 427/2.1; 424/429; 423/610
(58) Field of Classification Search
USPC ................ 623/11.11; 427/2.1, 2.24; 424/429, 424/618; 423/610
See application file for complete search history.

(56) References Cited

U.S. PATENT DOCUMENTS

| 6,482,444 | B1 | 11/2002 | Bellantone et al. |
| 2004/0126596 | A1 | 7/2004 | Zamora et al. |
| 2005/0008676 | A1* | 1/2005 | Qiu et al. .................. 424/429 |
| 2005/0013766 | A1* | 1/2005 | Imura et al. ................ 423/610 |
| 2006/0161256 | A1* | 7/2006 | Ziegler et al. ............. 623/11.11 |

FOREIGN PATENT DOCUMENTS

| EP | 1291033 | 3/2003 |
| WO | 01/45862 | 6/2001 |
| WO | PCT/EP03/10334 | * 9/2003 |
| WO | 2004/026346 | 4/2004 |
| WO | 2006/060734 | 6/2006 |

OTHER PUBLICATIONS

Babapulle et al., "Coated Stents for the Prevention of Restenosis: Part II", Circulation, Journal of the American Heart Association, 106, pp. 2859-2866, 2002.

(Continued)

*Primary Examiner* — Dah-Wei Yuan
*Assistant Examiner* — Andrew Bowman
(74) *Attorney, Agent, or Firm* — Cozen O'Connor

(57) ABSTRACT

Disclosed is a method for producing an implant coating that has a defined toxicity. The method is characterized by the following steps: i. a sol is produced from a biotoxic solution containing precious metal ions and a precursor solution for a titanium oxide; ii. an implant is coated by applying the sol in a sol-gel process; iii. the coating is pyrolyzed and sintered without admitting any light, the precious metal ion concentration in the dried coating ranging from 10 to 60 percent relative to the total weight of the dried coating; and iv. at least subareas of the coating produced without admitting any light are illuminated in order to reduce the toxicity of the dried coating to a predetermined measure.

8 Claims, 3 Drawing Sheets

OTHER PUBLICATIONS

Colombo et al., "Randomized Study to Evaluate Sirolimus-Eluting Stents Implanted at Coronary Bifurcation Lesions", Circulation, Journal of the American Heart Association, 109, pp. 1244-1249, 2004.

Edelman et al., "Gold-Coated NIR Stents in Porcine Coronary Arteries", Circulation, Journal of the American Heart Association, 103, pp. 429-434, 2001.

Galloni et al., "Carbon-Coated Stents Implanted in Porcine Iliac and Renal Arteries: Histologic and Histomorphometric Study", J. Vasc. Interv. Radiol, 14, pp. 1053-1061, 2003.

Kastrati et al., "Increased Risk of Restenosis After Placement of Gold-Coated Stents: Results of a Randomized Trial Comparing Gold-Coated with Uncoated Steel Stents in Patients with Coronary Artery Disease", Circulation, Journal of the American Heart Association, 101, pp. 2478-2483, 2000.

* cited by examiner ized by the present invention consists in the fact that only # IMPLANT COMPRISING A BIOTOXIC COATING AND METHOD FOR THE PRODUCTION THEREOF

CROSS-REFERENCE TO RELATED APPLICATIONS

This application represents a National Stage application of PCT/DE2008/000814 entitled "Implant Comprising a Biotoxic Coating and Method for the Production Thereof" filed May 13, 2008, pending.

BACKGROUND OF THE INVENTION

The invention relates to an implant comprising a biotoxic coating. The invention relates in particular to an implant with a titanium oxide coating containing silver ions, the silver ions being embedded into the coating by thermally sintering a precursor material. The invention further relates to a method for the production of an implant coating with a defined toxicity.

Among the problems of implant medicine is, as is known, the rejection reaction. To outwit the body's defenses, implants (for example pacemakers) are nowadays provided with biocompatible coatings on which a favorable environment for the proliferation of tissue cells predominates. This favors the implant growing in, which can additionally be supported by drugs.

Implants with a drug-releasing coating ("drug-eluting") have been suggested in the technical literature with a variety of objectives, and they partly already exist on the market. This concerns very particularly vascular prostheses, so-called stents.

In the case of stents, the problem is known that tissue can form and/or cells can build up on the inside of the stent which counters the purpose of the stent implantation and can have life-threatening consequences for the patient, for this can lead to inflammations or the inside of the stent being overgrown. This problem is particularly acute in the case of stents that have to be placed over vessel bifurcations, since then the subordinate vessels can no longer be supplied with blood in the case of an in-stent restenosis. Therefore a biotoxic coating of the inside of the stent is desirable that prevents cells from attaching themselves by being poisoned very slowly. Other cells moving passed (for example red blood cells in the blood stream) may of course not be affected.

It was suggested to prevent these inflammation and coagulation reactions in stents by local drug release. However, randomized studies have shown that in comparison to control groups (uncoated stents) the result was not significantly different [e.g. Antonio Colombo, Jeffrey W. Moses, Marie Claude Morice et al., "Randomized Study to evaluate Sirolimus-Eluting Stents at Coronary Bifurcation Lesions", Circulation 2004; 109:1244-1249].

At another place (galvanic) gold coating of coronary stents is reported on [Edelmann E R et al., "Gold-coated NIR stents in porcine coronary arteries", Circulation 2001; 103:429-434]. The in vivo tests did not show any improvement in animal tests compared to the control group. There were even reports on increased inflammation and in-stent restenosis in the case of gold-coated stents [Kastrati A et al., "Increased risk of restenosis after placement of gold-coated stents: results of a randomized trial comparing gold-coated with uncoated steel stents in patients with coronary artery disease", Circulation 2004; 101: 2478-2483].

Further studies report on carbon coatings (DLC) without any details on differences to control groups in animal tests [Galloni M, Prunotto M et al., "Carbon-coated stents implanted in porcine iliac and renal arteries: histological and histomorphic study", J. Vasc. Radiol. 2003; 14: 1053-1061; Ralf Max Beck, "Untersuchung von Ober-flächenbeschichtungen bei Gefäßstützen zur Reduktion von Restenosen", Thesis University of Tübingen 2001]. In an overview study, SiC, DLC and drug-coated stents were evaluated regarding to their effectiveness in reducing the in-stent restenosis rate [Babapulle M N, Eisenberg M J., "Coated stents for the prevention of restenosis: Part II", Circulation 2002; 106: 2859-2866]. It was shown that all coatings only have a marginal influence on the restenosis rate.

A stent coating may also not be damaged or even worn off slowly by the blood constantly flowing passed. On top of this, it should show a markedly reduced biotoxicity on the stent outside precisely in order to promote the growing-in of the implant. It was therefore already suggested to provide areas having differing biocompatibility on the same implant.

The specifications WO 01/45862 A1 and US 2004/0126596 A1 reveal the possibility of a plasma treatment of implant surfaces with the goal of preventing the proliferation of specific cells thereto or to achieve an apoptosis. It is in particular also suggested to deposit suitable monomers via plasma deposition so as to form biocompatible polymer layers on the substrates. Since in principle plasma methods can only be carried out in a vacuum or a protective-gas atmosphere, it is only the implant manufacturers that can be expected to have the required equipment and process know-how.

A complication in surgical operations where a stent is implanted can also be that for example a stent has to be inserted close to a vessel bifurcation in such a way that its outside is not totally flush with the vessel wall. If this outside has now been made biocompatible by pretreatment, then this again is favorable for cells adhering at an unintended location, that is to say in the blood stream in the area of the bifurcation.

It would therefore be desirable to have implant coatings that could be modified in terms of their biotoxicity by the medical staff after their manufacture and sale using simple means. This should be possible to happen by simple admission of energy (for example light, heat, electrical discharge or similar), it being possible for a simple handheld applicator to be a possible tool for functionalizing. As an example, reference is made to UV lamps in the dental practice, using which for example tooth fillings and the like can be cured in an accelerated manner.

In another, not pre-published application the inventor proposed a method for producing substrate coatings for surface-enhanced Raman spectroscopy (SERS) where by means of a sol-gel process a titanium oxide layer containing silver ions is at first produced that forms silver nanoparticles at the surface by subsequent irradiation with—predominantly visible—light while at the same time heating.

Even though it is known from the printed patent specification U.S. Pat. No. 6,482,444 B1 that sol-gel coatings with silver-containing glass ceramics have an antibacterial effect and above all improve tissue adherence and inhibit inflammations in the case of bone and joint implants. However, silver is a known cell toxin and not to be recommended a priori for biocompatible implants.

SUMMARY OF THE INVENTION

The invention is therefore based on the objective of creating a robust implant coating that has a high degree of biotoxicity immediately after its production, that can be modified in a simply way by subsequent processing, that is to say in particular on predetermined subareas.

This objective is achieved in multiple ways, including a method for producing an implant coating with a defined toxicity and with certain features, providing an implant with the features and through advantageous implementation of the invention.

According to the invention, a titanium oxide layer containing silver ions is produced on the implant that really has—as is evident—a biotoxic effect. According to the invention, the implant coating so produced is furthermore post-treated at a later point in time, in particular before and during a surgical operation on a patient, at least on subareas, by means of irradiation while heating it at the same time, so that the biotoxicity is markedly reduced on these subareas.

It is provided, that the subareas having reduced biotoxicity can be determined by the doctor giving the treatment in such a way that they correspond to the subareas of the implant where it is desired medically that the surrounding tissue builds up. To this end, he advantageously has the knowledge of the specific patient and of the details of the operation at his disposal. This information was of course not known at the time of the production of the implant or the production of the coating.

BRIEF DESCRIPTION OF THE DRAWINGS

The invention is explained below in more detail. In the drawings.

DETAILED DESCRIPTION OF THE INVENTION

Figure 1:
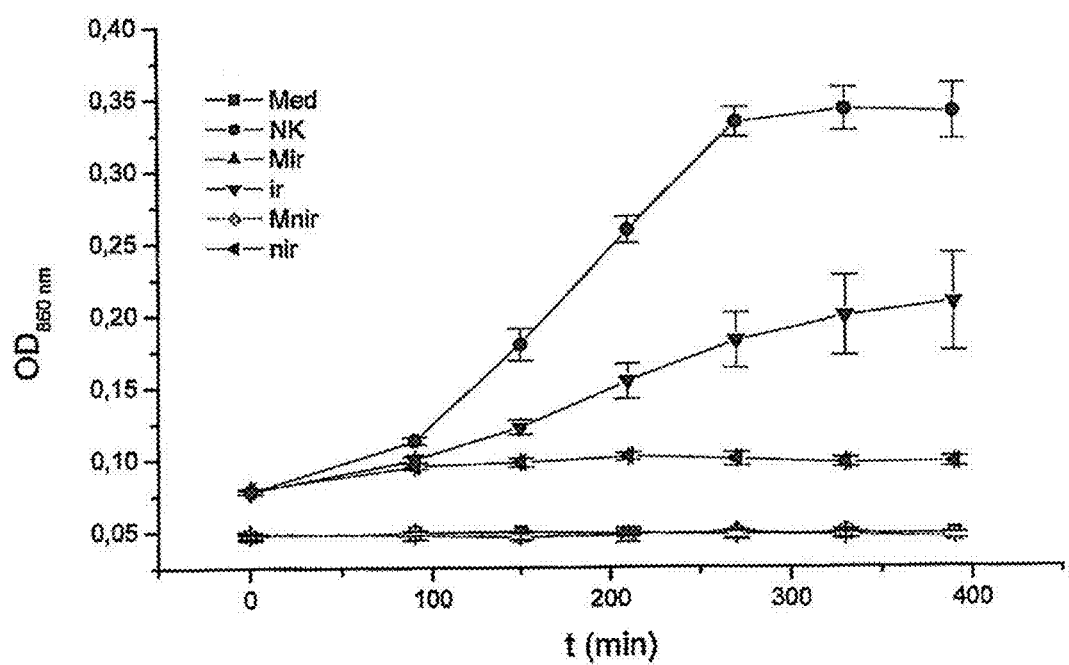
FIG. 1 shows a comparison of the bactericidal action of irradiated (ir) and non-irradiated (nir) SER layers on contacting suspension cultures (Med: medium; Mir: medium with irradiated SER layer; Mnir: medium with non-irradiated SER coating; NK: bacterial culture without layer)

The inventive implant coating is formed in the following way:

Continuing on from the teachings of WO 2006/060734 A2, here, too, the starting point is a precursor that contains additional precious metal ions for the production of a metal oxide film by means of a sol-gel process. However, the precursor has to contain titanium for the invention to be realized, so that a titanium oxide matrix can be formed, preferably $TiO_2$.

Particularly preferably silver ions are used as precious metal ions. Even though other precious metals shall not be excluded, however no studies exist for this so far.

The invention further develops the known method in an unexpected manner, in that the titanium precursor containing silver ions is at first applied to a heat-resistant substrate (for example glass, semiconductor, metal) using a sol-gel process (in particular spinning, spraying, dipping) and is pyrolyzed and sintered there immediately without admitting any light. After the heat treatment the layer is dry and hard and largely resistant against any chemical attack. It has virtually no silver nanoparticles on the surface and is therefore not suitable as an SER substrate. A further treatment according to the teachings of WO 2006/060734 A2 is also not suited to improve this. The layer has a very good shelf-life when it is stored without admitting any light.

If the titanium oxide layer that contains silver is now irradiated intensively by also being heated sufficiently, then electron-hole pairs are produced in the matrix according to

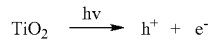

Silver ions that are present have a strong tendency to absorb the electrons that have been released.

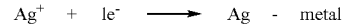

Tiny silver particles are formed that exhibit a certain mobility in the matrix that is heated at the same time. By diffusion, they can also combine to form larger particles. Silver in the immediate vicinity of the layer surface penetrates it and forms silver nanoparticles on the surface. If the silver-titanium oxide nanocomposite thus produced is again cooled to ambient temperature, the silver particle distribution is practically "frozen". The layer was previously SER-inactive and has been treated with light and heat is then suited as SER substrate and at the same time shows an amplification factor that can compete with commercially available substrates.

First of all a $TiO_2$—Ag precursor solution (sol) is produced. The silver contents should be between 10% and 60% by weight relative to the total weight of the dried layer (after pyrolysis and sintering). The Ag mass fraction is preferably adjusted between 30% and 60%. In the following example it is approximately 50%, which is to be regarded as particularly favorable.

For preparing 100 ml of an approximately 0.6 mol solution, at first 10 ml of 2-methoxyethanol and acetylacetone are put in a beaker. Then the Ti-isopropoxide is added, after which stirring is carried out for 30 minutes. As a second solution, 10 ml of 2-methoxyethanol are mixed with water. After 30 minutes of stirring, the water-containing solution is added to the Ti-acetylacetone complex. This is again stirred for 30 minutes. For the silver solution, 10 ml of 2-methoxyethanol are put in a beaker and $AgNO_3$ and pyridine (as stabilizer) are added. This complex likewise has to be stirred for 30 minutes. Then the silver solution can be added to the stabilized and hydrolyzed titanium solution. After again stirring for 30 minutes, 2 g of polyethylene glycol 400 are added to the solution, topped up to 100 ml with 2-methoxyethanol and then filtered. The polyethylene glycol serves to form a layer without cracks. The ranges of the weighed portions, that is to say the mol percentages, can be gathered from the following table.

| Product | Educt | Mol | In g as an example |
|---|---|---|---|
| $TiO_2$—50%Ag | TiIVPropoxid $Ti(OCHMet_2)_4$ | 0.03-0.05 | 9.83 |
| | $AgNO_3$ | 0.01-0.03 | 4.33 |
| | Methoxyethanol | 0.5-0.7 | 52.23 |
| | $H_2O$ | 0.05-0.2 | 2.48 |
| | Acetylacetone | 0.01-0.03 | 1.73 |
| | Pyridine | 0.1-0.5 | 30.26 |
| | PEG400 | — | 2.00 |

Ti-iso.=Ti-isopropoxide
Hacac=Acetylacetone
  Stoichiometries used:
  Ti-isoprop.: Hacac: $H_2O$=1:0.5:4 (mol)
  $AgNO_3$: pyridine=1:15 (mol)

The TiO₂—Ag layers are produced by dip coating. The carrier used is for example implant steel. Pyrolyzing the layers is then carried out at 250° C. The final treatment temperature (sintering step) is between 450 and 550° C. The thickness of the layers can amount to between 50 and 100 nm. During the thermal treatment, absolute care has to be taken that it is carried out without admitting any light (UV up to the end of VIS). Only in this way, any uncontrolled settling/reduction of silver is avoided.

After the production, the implants can be irradiated immediately or, as the case may be, also be stored in darkness. Irradiation can take place with virtually all conventional lamps that emit light in the spectral range from 280 to 800 nm. The TiO₂ matrix absorbs very well in the entire visible range, this being the reason why TiO₂ is also known as solar absorber. If in the process the lamp at the same time emits heat that heats up the layer, the SER activation can already be set in motion by forming the silver particles on the layer surface. As an alternative, it is also possible to use light sources with a lower power (for example laser or luminescent diodes) in combination with a heat source that permits a temperature of up to 250° C.

The particle size and distribution are adjusted by the combined action of irradiation and heat. The irradiation leads to the silver being reduced from silver oxide into elemental silver, and the heat leads to the particles becoming coarser by diffusion.

For this purpose, the input of heat should be adjusted in such a way that the layer has at least temperatures above 80° C. Temperatures between approximately 150° C. and 250° C. are to be preferred. It has however turned out to be not advantageous to use temperatures above 250° C., since the mobility of the silver particles would otherwise become too high. The result could be particle distributions on the layer surface that are rather non-uniform and that adversely affect the SER activity.

In summary, the layer has the following advantages compared to the state of the art:
- only industrial standard processes are used (sol-gel coating, pyrolysis, masking, irradiation) that can be carried out at a correspondingly high speed.
- titanium oxide layers are often used and are known to be chemically stable. Disposal channels for used SER substrates therefore also already exist.
- apart from the inevitable burning-out of the organic components during pyrolysis, no further chemicals are used and released, that is to say, no new disposal problem is created.
- the reproducibility of the SER substrates is—as always—a question of the precise process control. The processes employed here are without exception controlled in industry and require no new developments.

The abrasion-proof biotoxic coating that is aimed at, having a titanium oxide layer that contains silver ions is characterized in that the silver ions are embedded on intercalation sites in the matrix by thermal sintering a precursor material without admitting any light and can be reduced by exposure to light.

The embedded silver ions can be present by irradiation with UV light while converting into less biotoxic silver nanoparticles for releasing electron-hole pairs in the titanium oxide matrix so that layers can be achieved in which predetermined regions are strongly reduced in terms of their biotoxicity by UV irradiation during the course of several minutes compared to a non-irradiated titanium oxide layer that still contains silver ions, in that the ions have been converted in small metallic silver particles by diffusion.

For a coating a titanium precursor that contains silver ions is therefore at first applied to the implant surface in a sol-gel process (in particular spinning, spraying, immersion) and there pyrolyzed and sintered immediately without admitting any light. In the process, it is assumed for the implant material that it is resistant to temperatures for heat treatment (up to approximately 600° C.), for example implant steel. After the heat treatment, the produced titanium oxide layer with silver ions contained therein is dry and hard and largely resistant to a chemical attack. It is robust against abrasion and preferably covers the whole surface of the implant.

The implant with the inventive SER layer is proven to be biotoxic, as is explained further below. The SER layer maintains its properties even over a long time when the implant is stored without admitting any light (it is packed in a light-tight manner).

If the silver-containing titanium oxide layer is irradiated, electron-hole pairs are produced in the matrix and silver ions that are present have a large tendency to receive the released electrons, and tiny silver particles form in the process that grow by solid-state diffusion—that is preferably during heating—to form larger particles.

When the silver titanium oxide nanocomposite that has now been produced is again cooled to ambient temperature, the silver particle distribution is practically "frozen". The SER layer that was previously biotoxic and has been treated with light and heat exhibits a markedly reduced biotoxicity after this treatment.

The cause of the biotoxicity of the layer that has been produced first could be the ability for emitting silver ions to cells (or also bacteria) that are possibly in contact with the layer. This cell toxin emission prevents the proliferation. After the irradiation a large part of the silver is present in reduced metallic form as nanoparticles. These particles are moreover to a large extent not present at the surface, but continue to lie embedded in the titanium oxide matrix. The ability of the SER layer to emit silver ions is thus reduced very strongly, and the biotoxicity decreases.

A layer that has been prepared with 9.8 g (that is to say 0.035 mol) of TiIVpropoxide educt, 4.3 g of AgNO₃ (see Table) can for example be irradiated immediately after the preparation or, as the case may be, can also be stored in darkness. The irradiation can take place with virtually all conventional lamps that emit light in the spectral range from 280 to 800 nm. The TiO₂—Ag layer absorbs very well in the entire visible range, this being the reason why TiO₂ is also know as solar absorber.

However, what is preferred here is the use of a UV lamp having wavelengths in the range from 250 to 400 nm (for example a power of 100 W). The SER layer should be heated to temperatures of approximately 80° C. which can already take place by the irradiation of the UV lamp. Typical treatment times are preferably approximately 20 minutes.

The particle size and distribution are adjusted by the combined action of irradiation and heat. The irradiation leads to the silver being reduced from silver oxide into elemental silver, and the heat leads to the particles becoming coarser by diffusion.

Biotoxicity tests are carried out on the SER layers that have been prepared.

The bactericidal effect of irradiated and non-irradiated SER layers is tested on an alpha-haemolyzing Streptococcus mixed culture (apathogene), obtained from the throat swab of a healthy donor. To this end, the bacterial growth at 38° C. is determined photometrically at 860 nm by turbidimetric measurement. The result is shown in FIG. 1. The optical density (OD) of the bacterial culture is plotted as a function of the time. The culture without an SER layer (NK) shows the strongest turbidity, that is to say maximum growth. The curves of the lowest turbidity (Med, Mir, Mnir) did not show any bacterial cultures, but only the suspension medium without or with SER layer (irradiated, not irradiated) as a reference. The relevant measurement curves (ir, nir) describe the behavior of the bacterial growth on the irradiated and the non-irradiated SER layer respectively. This reveals that the optical density for the culture on the irradiated SER layer is approximately halved with respect to the pure culture without SER layer, that is to say even the irradiated SER layer still has a biotoxic effect. However, its biotoxicity is strongly reduced relative to the non-irradiated SER layer which can be clearly seen from the reduction of the optical density of the culture by a further 60% on the non-irradiated layer.

The change in the biotoxicity of the SER layer becomes still clearer when the cell proliferation is examined. The BrdU (r-bromo-2'deoxy-uridine) test enables the cell proliferation of cell cultures (in our case primary fibroblasts from passage 2 to 4 from a healthy donor), grown in well plates, to be quantified by means of the BrdU built into the DNA of the cell. A medium that contains BrdU is added to the cells. Proliferating cells incorporate the BrdU addition instead of thymidine (a component of the DNA) into their DNA. After incubation times from 4 to 24 hours the medium is removed, the cells are washed and fixated. This achieves a more simple access to the BrdU which is detected by a specific antibody carrying a marker enzyme (peroxidase). Marked antigene antibody complexes are formed. If the substrate of the marker enzyme is now added to these complexes, in our case ABTS, a reaction then takes place in which the substrate is transformed into the oxidized form. The oxidized form of ABTS is present in the dissolved form and has a green-blue color. The optical density of the solution can be measured photometrically at 405 nm (reference: 490 nm). This permits conclusions to be drawn as to the amount of incorporated BrdU and thus to the proliferation.

Figure 2:
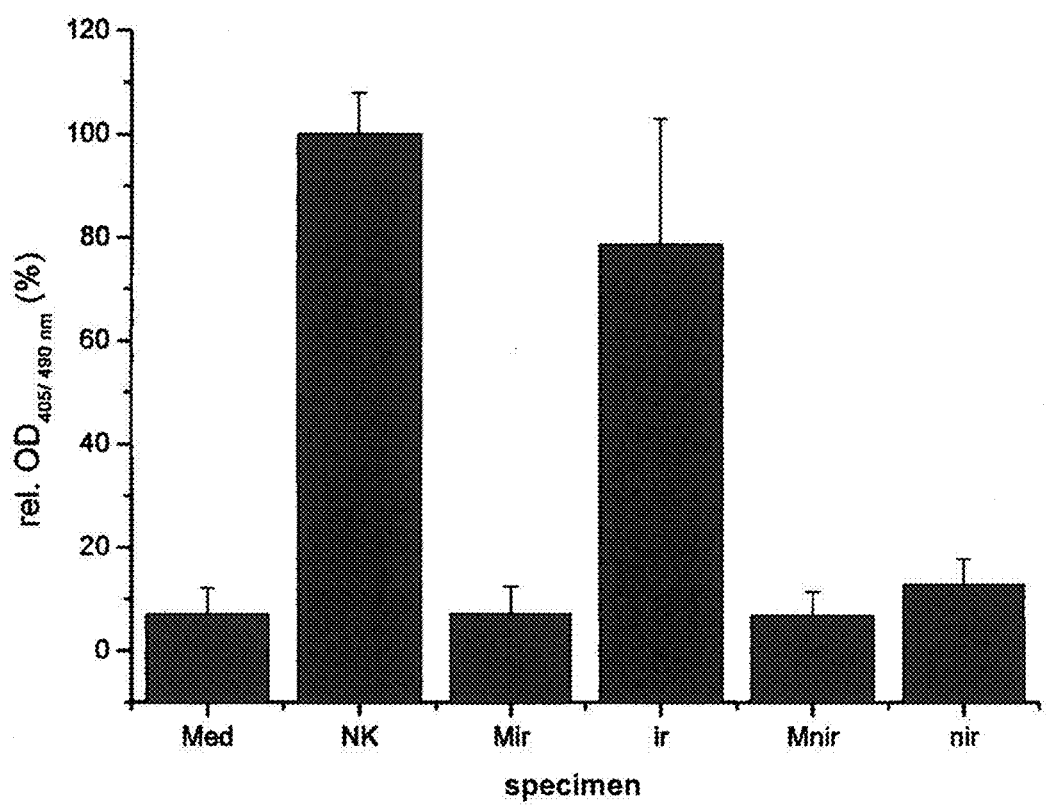
FIG. 2 show results of cell proliferation study by means of BrdU test (abbreviations analogous to FIG. 1)

The ratio of the optical densities (rel. OD) at 405 nm and 490 nm is measured as a degree for the cell proliferation. The result is shown in FIG. 2 as a histogram. The legend of the histogram columns has basically the same meaning as in FIG. 1. It should be emphasized here that the cell proliferation on the irradiated SER layer is only reduced by approximately 20%, while it is inhibited almost completely on the non-irradiated SER layer.

Figure 3:
FIG. 3 shows a cell culture at the boundary between irradiated and non-irradiated regions of the inventive SER coating on an implant steel.

By means of light microscopy of colored (Giemsa coloring) specimens the cell morphology is finally also investigated at the boundary between irradiated and non-irradiated SER layer. For this purpose, 24-hour-cultures of primary fibroblasts of passage 2 to 4 are prepared on partially irradiated surfaces. After incubation has been carried out (in 5% $CO_2$ at 38° C.), the cells are fixated with glutaraldehyde and colored with Giemsa. The visible results for irradiated surfaces that have been irradiated in a masked fashion (irradiation with UV (250-400 nm) for 20 minutes before cell cultivation) can be seen in FIG. 3; left side: irradiated, right side: non-irradiated). In the irradiated region, a markedly more dense growth with elongate, screw-shaped fibroblasts can be seen, while only a few shortened and dead cells are visible in the non-irradiated region.

The invention claimed is:

1. A method of producing an implant with a coating whose toxicity can be adjusted, the method comprising the steps of:
   i. producing a sol from a biotoxically acting solution that contains precious metal ions, and a precursor solution for a titanium oxide;
   ii. coating an implant by applying the sol with a sol-gel process;
   iii. pyrolyzing and sintering the coating without admitting any light, so as to form a dried coating; wherein
   the proportion of the precious metal ions in the dried coating being between 10 and 60% of a total mass of the dried coating,
   additionally comprising the steps of irradiating at least subareas of the coating for reducing the toxicity of the dried coating to a predetermined degree wherein the coating that has been produced without admitting any light is partially covered with an opaque template that has cutouts before being irradiated.

2. The method according to claim 1, wherein the irradiation step takes place while at least the irradiated subareas are heated at the same time.

3. The method according to claim 1, wherein the irradiation of the coating produced without admitting any light is carried out simultaneously on a multiplicity of spatially separate subareas.

4. The method according to claim 1, wherein, between the pyrolyzing and sintering without admitting any light and the irradiating of the coating that has been produced without admitting any light, a storage time without admitting any light is provided.

5. The method according to claim 1, wherein the irradiation of the coating that has been produced without admitting any light is carried out while heating at least the irradiated subareas to temperatures of between 80° C. and 250° C.

6. The method according to claim 1, wherein silver ions are used as the precious metal ions, and the silver percentage relative to the total mass of the dried coating is adjusted to between 30 and 60%.

7. The method according to claim 1, wherein the pyrolyzing step is performed at temperatures of about 250° C. without admitting any light and the sintering step is performed at temperatures of between 450° C. and 550° C. without admitting any light.

8. The method according to claim 6, additionally comprising stabilizing the sol containing silver ions by adding pyridine.

* * * * *